US009012602B2

(12) United States Patent
Naso et al.

(10) Patent No.: US 9,012,602 B2
(45) Date of Patent: Apr. 21, 2015

(54) *MACACA FASCICULARIS* CCL17

(75) Inventors: Michael Naso, Radnor, PA (US); Mary Ryan, Radnor, PA (US); Sandra Santulli-Marotto, Radnor, PA (US); Bethany Swencki-Underwood, Radnor, PA (US)

(73) Assignee: Janssen Biotech, Inc., Horsham, PA (US)

( * ) Notice: Subject to any disclaimer, the term of this patent is extended or adjusted under 35 U.S.C. 154(b) by 50 days.

(21) Appl. No.: 13/245,349

(22) Filed: Sep. 26, 2011

(65) Prior Publication Data

US 2012/0082622 A1 Apr. 5, 2012

Related U.S. Application Data (60) Provisional application No. 61/386,695, filed on Sep. 27, 2010, provisional application No. 61/391,288, filed on Oct. 8, 2010.

(51) Int. Cl.
*C07K 14/52* (2006.01)

(52) U.S. Cl.
CPC ............. *C07K 14/523* (2013.01); *C07K 14/521* (2013.01); *C07K 2319/00* (2013.01); *C07K 2319/30* (2013.01); *Y10S 530/866* (2013.01)

(58) Field of Classification Search
None
See application file for complete search history.

(56) References Cited

U.S. PATENT DOCUMENTS

| | | | |
|---|---|---|---|
| 2006/0234972 | A1 | 10/2006 | Karras et al. |
| 2007/0072175 | A1 | 3/2007 | Cooper et al. |
| 2007/0212301 | A1 | 9/2007 | Aldrich et al. |
| 2009/0291455 | A1 | 11/2009 | Naso et al. |

FOREIGN PATENT DOCUMENTS

| | | |
|---|---|---|
| WO | WO 2006/102395 A2 | 9/2006 |
| WO | WO 2009/086514 A1 | 7/2009 |

OTHER PUBLICATIONS

Basu et al. Molecular cloning and sequencing of 25 different *Rhesus macaque* chemokine cDNAs reveals evoluationary conservation aminog C, CC, CXC, and CX3C families of chemokines. Cytokine 18(3): 140-148, 2002.*
Basu et al. UniProtKB/Swiss-Prot Accession No. Q8HYP9; Mar. 1, 2003, 3 pages.*
Belperio, et al., "The Fole of the Th2 CC Chemokine Ligand CCL17 in Pulmonary Fibrosis," Journal of Immunology, 173: 4692-4698 (2004).
Campbell, et al., "The chemokine receptor CCR4 in vascular recognition by cutaneous but not intestinal memory T cells," Nature, 400: 776-780 (1999).
Imai et al., "Molecular cloning of a novel T cell-directed CC chemokine expressed in thymus by signal sequence trap using Epstein-Barr virus vector," Journal of Biological Chemistry, 271: 21514-21521 (1996).
Jahnz-Rozyk, et al., "Serum thymus and activation-regulated chemokine, macrophage-derived chemokine and eotaxin as markers of severity of atopic dermatitis," Allergy, 60: 685-688 (2005).
Katakura, et al., "CCL17 and IL-10 as Effectors That Enable Alternatively Activated Macrophages to Inhibit the Generation of Classically Activated Macrophages," The Journal of Immunology, 172: 1407-1413 (2004).
Kawasaki, et al., "Intervention of thymus and Activation-Regulated Chemokine Attenuates the Development of Allergic Airway Inflammation and Hyperresponsiveness in Mice," The Journal of Immunology, 166: 2055-2062 (2001).
Leung, et al., "Plasma TARC concentration may be a useful marker for asthmatic exacerbation in children," European Respiratory Journal, 21: 616-620 (2003).
Sallusto et al., "Distinct patterns and kinetics of chemokine production regulate dendritic cell function," European Journal of Immunology, 29: 1617-1625 (1999).
Sekiya et al., "Inducible expression of a Th2-type CC chemokine thymus- and activation-regulated chemokine by human bronchial epithelial cells," Journal of Immunoogy, 165: 2205-2213 (2000).
Wenzel, et al., "Role of the Chemokine Receptor CCR4 and its ligand Thymus-and Activation-Regulated Chemokine/CCL17 for Lymphocyte Recruitment in Cutaneous Lupus Erythematosus," Journal of Investigative Dermatology, 124: 1241-1248 (2005).
GenBank Acc. No. NM_001032852, 2002.
PCT International Search Report dated Feb. 23, 2012 for PCT/US2011/053255.
Qin, et al., "Chemokine and Cytokine Mediated Loss of Regulatory T Cells in Lymph Nodes during Pathogenic Simian Immunodeficiency Virus Infection," The Journal of Immunology, 180:5530-5536 (2008).
UniProt Accession No. Q8HYP9, Retrieved on Jan. 19, 2012.
Supplementary European Search Report dated Feb. 11, 2014 for EP 11831245.
Moxley, et al., "Cloning and pharmacological characterization of CCR7, CCL21 and CCL19 from *Macaca fascicularis*," European Journal of Pharmaceutical Sciences, 37:264-271 (2009).
UniProt Accession No. AF449271, Last Updated Oct. 7, 2008.
Search Report from State Intellectual Property Office of People's Republic of China dated Jul. 3, 2014.

\* cited by examiner

*Primary Examiner* — Bridget E Bunner
(74) *Attorney, Agent, or Firm* — Kirk Baumeister (57) ABSTRACT

Isolated polynucleotides encoding *Macaca fascicularis* CCL17 (CynoCCL17), polypeptides obtainable from expression of these polynucleotides, recombinant cells, and methods of use are disclosed.

2 Claims, 2 Drawing Sheets

Figure 1

```
cynoCCL17
MAPLKMLALVILLLGVALVTLLLGASLQHIHAARGTNVGRECCLKYFKGAIPLRKLKTWY
huCCL17         MAPLKMLA---------
LVTLLLGASLQHIHAARGTNVGRECCLEYFKGAIPLRKLKTWY
                ********
******************************:************* cynoCCL17       QTSEDCSRDAIVFVTVQNKAICSDPNDKKVKKALKYLQSL---
huCCL17         QTSEDCSRDAIVFVTVQGRAICSDPNNKRVKNAVKYLQSLERS
                ****************.:********:*:**:*:******
```

MACACA FASCICULARIS CCL17

CROSS-REFERENCE TO RELATED APPLICATIONS

This application claims the benefit of U.S. Provisional Application Ser. Nos. 61/386,695, filed 27 Sep. 2010 and 61/391,288, filed 8 Oct. 2010, the entire contents of which are incorporated herein by reference in their entirety.

FIELD OF THE INVENTION

The present invention relates to *Macaca fascicularis* (cynomolgus) CCL17 and its uses.

BACKGROUND OF THE INVENTION

CCL17 (thymus and activation regulated chemokine, TARC), is a chemokine ligand for CCR4. CCL17 is constitutively expressed in thymus, and upon activation is produced by a number of cellular sources, including PBMCs, monocytes, macrophages, dendritic, endothelial, and bronchial cells (Imai et al., J Biol Chem, 271:21514-21, 1996; Sallusto et al., Eur J Immunol, 29:1617-25, 1999; Campbell et al., Nature, 400:776-80, 1999; Sekiya et al., J Immunol, 165: 2205-13, 2000).

CCL17 induces chemotaxis of CCR4 expressing cells (mainly Th2 and cutaneous T lymphocytes), and is thus implicated in the maintenance of Th2 immune responses (Imai et al., Int Immunol, 11:81-8, 1999), as well as in the suppression of classically-activated macrophages (Katakura et al., J Immunol, 172:1407-13, 2004). Neutralization of CCL17 has been shown to reduce Th2 cytokines, airway eosinophilia and hyperresponsiveness in allergen-induced asthma (Kawasaki et al., J Immunol, 166:2055-62, 2001), and protect from pulmonary fibrosis (Belperio et al., J Immunol, 173:4692-8, 2004). CCL17 expression levels correlate with the disease phenotype in chronic allergic pathologies, including asthma (Leung et al., Eur Respir J, 21:616-20, 2003), atopic dermatitis (Jahnz-Rozyk et al., Allergy 60:685-8, 2005) and cutaneous lupus erythematosus (Wenzel et al., J Invest Dermatol, 124:1241-8, 2005). Thus, modulators of CCL17 signaling, such as neutralizing anti-CCL17 antibodies, may have a therapeutic benefit for inflammatory, allergic, and fibrotic conditions.

Predictive pharmacokinetic, safety and efficacy studies will be required before any CCL17 modulator for human use can be brought to the market place. Such studies will involve both in vitro and in vivo testing in animal models of CCL17-associated pathologies. Lack of cross-reactivity of the modulators with human CCL17 orthologs can pose a challenge in these studies. Thus, use of, antibody-based CCL17 modulators may require evaluation of cross-reactivity of the antibodies across species, generation of surrogate antibodies against a CCL17 polypeptide expressed by a particular model animal, as well as significant in vitro characterization of such surrogate antibodies. Evaluation of cross-reactivity, surrogate generation and in vitro characterization will require the use of CCL17 polynucleotides and polypeptides from a suitable animal model.

Thus, a need exists for the identification of polynucleotides encoding CCL17 and CCL17 polypeptides being expressed in an animal model identified as suitable for the predictive pharmacokinetic, safety and efficacy studies of CCL17 modulators. A need also exists for related methods such as methods of expressing such polypeptides and testing the cross-reactivity of CCL17 modulators.

SUMMARY OF THE INVENTION

One aspect of the invention is an isolated polynucleotide encoding a polypeptide comprising the amino acid sequence shown in SEQ ID NO: 1.

Another aspect of the invention is an isolated polynucleotide encoding a polypeptide having the amino acid sequence shown in SEQ ID NO: 3.

Another aspect of the invention is a vector comprising an isolated polynucleotide of the invention.

Another aspect of the invention is a host cell comprising the vector of the invention.

Another aspect of the invention is an isolated polypeptide comprising a polypeptide having the sequence shown in SEQ ID NO: 1.

Another aspect of the invention is an isolated polypeptide having the sequence shown in SEQ ID NO: 3.

Another aspect of the invention is a method for expressing a polypeptide comprising the steps of: providing the host cell of the invention; and culturing the host cell under conditions sufficient for the expression of at least one polypeptide of the invention.

Another aspect of the invention is an isolated antibody that specifically binds the polypeptides of the invention.

Another aspect of the invention is a method for determining cross-reactivity of a human CCL17 modulator with *Macaca fascicularis* CCL17 comprising: providing a CCL17 modulator and a *Macaca fascicularis* CCL17 isolated polypeptide of the invention; contacting the CCL17 modulator with the *Macaca fascicularis* CCL17 isolated polypeptide; and determining whether the CCL17 modulator binds to the *Macaca fascicularis* CCL17 isolated polypeptide.

Another aspect of the invention is a method for determining cross-reactivity of a human CCL17 modulator with *Macaca fascicularis* CCL17, comprising: providing a CCL17 modulator and a *Macaca fascicularis* CCL17 isolated polypeptide of the invention; providing a cell expressing CCR4; contacting the cell expressing CCR4 with the CCL17 modulator and the *Macaca fascicularis* CCL17 polypeptide; and determining the effect of the CCL17 modulator on a CCL17 biological activity, wherein modulation of the CCL17 biological activity shows that the CCL17 therapeutic cross-reacts with the *Macaca fascicularis* CCL17.

Another aspect of the invention is a method for assessing the safety of a CCL17 modulator comprising: providing a CCL17 modulator, a first *Macaca fascicularis* monkey, and a second *Macaca fascicularis* monkey; administering the CCL17 modulator to the first *Macaca fascicularis* monkey; and determining whether the first *Macaca fascicularis* monkey is presenting a deleterious symptom relative to the second monkey, where presentation of a deleterious symptom by the first *Macaca fascicularis* monkey shows the CCL17 modulator is potentially unsafe for use in humans and a lack of presentation of a deleterious symptom by the first *Macaca fascicularis* monkey shows the CCL17 therapeutic is potentially safe for use in humans.

DETAILED DESCRIPTION OF THE INVENTION

All publications, including but not limited to patents and patent applications, cited in this specification are herein incorporated by reference as though fully set forth.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "complementary sequence" means a second isolated polynucleotide sequence that is antiparallel to a first isolated polynucleotide sequence and that comprises nucleotides complementary to the nucleotides in the first polynucleotide sequence.

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "polypeptide" or "protein" means a molecule that comprises at least two amino acid residues linked by a peptide bond to form a polypeptide. Small polypeptides of less than 50 amino acids may be referred to as "peptides".

The term "antibody" includes whole antibodies and any fragments thereof. Antibody fragments comprise at least a portion of an immunoglobulin molecule, such as a complementarity determining region (CDR), a variable region, a constant region, or a framework region from either antibody heavy or light chain. An antibody may be a Fab, F(ab'), F(ab')$_2$, scFv, dsFv, or diabody. An antibody may be chimeric, humanized, or human antibody, dimeric, tetrameric or multimeric. Structures of the above mentioned antibody fragments, and techniques for the preparation and use of the antibodies and fragments thereof are well known in the art (Ausubel, et al., ed., Current Protocols in Molecular Biology, John Wiley & Sons, Inc., NY 1987-2001; Sambrook, et al., Molecular Cloning: A Laboratory Manual, $2^{nd}$ Edition, Cold Spring Harbor, N.Y., 1989; Harlow and Lane, Antibodies, a Laboratory Manual, Cold Spring Harbor, N.Y., 1989; Colligan, et al., ed., Current Protocols in Immunology, John Wiley & Sons, Inc., NY 1994-2001; Colligan et al., Current Protocols in Protein Science, John Wiley & Sons, NY, N.Y., 1997-2001; Kohler et al., Nature, 256:495-497, 1975; Queen et al., Proc Natl Acad Sci, 86:10029-33, 1989; U.S. Pat. No. 4,816, 567). For example, fully human monoclonal antibodies can be prepared from transgenic mice expressing human immunoglobulins or from phage display libraries (Lonberg et al., Nature, 368:856-9, 1994; Fishwild et al., Nature Biotech, 14:845-51, 1996; Mendez et al., Nature Genetics, 15:146-56, 1997; Knappik et al., J Mol Biol, 296:57-86, 2000; Krebs et al., J Immunol Meth, 265:67-84, 2001).

The term "deleterious symptom" means any symptom presented by an animal that indicates harm to the animal has occurred.

The term "modulator" means a molecule or preparation that is believed to provide a therapeutic benefit in humans or other animals at least in part by activating or suppressing CCL17 biological activity. Examples of CCL17 therapeutics include anti-CCL17 antibodies, antibody fragments, peptides, polypeptides, oligonucleotides, low molecular weight chemical compounds and the like. Known CCL17 modulators are for example siRNA molecules disclosed in U.S. Pat. No. 7,585,968 or monoclonal antibodies disclosed in (Morita et al. Clinica Chimica Acta, 322:67-75, 2002).

"Modulation of CCL17 biological activity" means partially or completely inhibiting, activating, or enhancing CCL17 biological activity.

"CCL17 biological activity" as used herein refers to any activity in a cell occurring as a result of CCL17 binding to its receptor CCR4. An exemplary CCL17 biological activity results in the induction of intracellular calcium flux upon receptor binding, which can be measured using calcium sensitive dyes such as Fluo-8 using routine methods (Imai et al., J Biol Chem, 272:15036-42, 1997). CCL17 biological activity can also be monitored by measuring for example T lymphocyte migration in response to CCL17 using established methods (Imai et al., J Biol Chem, 272:15036-42, 1997). Suitable cell lines that can be used are any cell line endogenously or recombinantly expressing CCR4 such as CCRF-CEM, Jurkat or Hut78.

The present invention provides isolated *Macaca fascicularis* (cynomolgus) CCL17 (cynoCCL17) polynucleotides, vectors comprising these polynucleotides, isolated host cells, polypeptides obtainable from expression of these polynucleotides, methods for expressing the polypeptides of the invention, and methods of using the polynucleotides and polypeptides of the invention.

The polynucleotides and vectors of the invention can be used to express cynoCCL17 polypeptides. CynoCCL17 polypeptides can be used to generate therapeutic antibodies for the suppression of the activity of cynoCCL17 or CCL17 from other species. CynoCCL17 polypeptides can also be used in in vitro or in vivo assays to identify other therapeutics such as small molecules or peptides capable of modulating the activity of cynoCCL17 or CCL17 from other species. Other methods disclosed are useful for assessing safety and cross-reactivity of a CCL17 therapeutic between animal species.

The full-length cynoCCL17 polypeptide sequence of the invention (SEQ ID NO: 1) is 84% identical and 89% similar to the human CCL17 polypeptide (SEQ ID NO: 5), allowing predictive pharmacokinetic, safety and efficacy studies of CCL17 therapeutics, and other uses.

One aspect of the invention is an isolated polynucleotide comprising a polynucleotide having the sequence shown in SEQ ID NO: 2, 4 or 13, or complementary sequences thereof. The polynucleotide sequence shown in SEQ ID NO: 2 encodes a polypeptide comprising the full length cynoCCL17. The polynucleotide sequence shown in SEQ ID NO: 4 encodes a polypeptide comprising the mature cynoCCL17. The polynucleotide sequence shown in SEQ ID NO: 13 encodes the mature cynoCCL17 and is codon-optimized for protein expression in *E. coli*.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR followed by routine cloning. Techniques for producing or obtaining polynucleotides of a given known sequence are well known in the art.

The polynucleotides of the invention may also comprise at least one non-coding sequence, such as ribosome binding sites, mRNA stabilizing sequences, introns and polyadenylation signals. The polynucleotide sequences may also comprise additional sequences encoding additional amino acids. These additional polynucleotide sequences may, for example, encode a marker or a tag sequence such as a hexa-histidine an HA tag to facilitate purification or detection of the protein.

Another embodiment of the invention is a vector comprising an isolated polynucleotide having a sequence shown in SEQ ID NO: 2, 4, or 13. The vectors of the invention are useful for maintaining polynucleotides, duplicating polynucleotides, or driving expression of a polypeptide encoded by a vector of the invention in biological systems, including reconstituted biological systems. Vectors may be chromosomal-, episomal- and virus-derived such as vectors derived from bacterial plasmids, bacteriophages, transposons, yeast episomes, insertion elements, yeast chromosomal elements, baculoviruses, papova viruses such as SV40, vaccinia viruses, adenoviruses, fowl pox viruses, pseudorabies viruses, picornaviruses and retroviruses and vectors derived from combinations thereof, such as cosmids and phagemids.

The vectors of the invention can be formulated in microparticles, with adjuvants, lipid, buffer or other excipients as appropriate for a particular application.

In one embodiment of the invention the vector is an expression vector. Expression vectors typically comprise nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art. Nucleic acid sequence elements and parent vector sequences suitable for use in the expression of encoded polypeptides are also well known. An exemplary plasmid-derived expression vector useful for expression of the polypeptides of the invention comprises an *E. coli* origin of replication, an aph(3')-1a kanamycin resistance gene, HCMV immediate early promoter with intron A, a synthetic polyA sequence and a bovine growth hormone terminator. Another exemplary plasmid derived expression vector comprises an *E. coli* origin of replication, an ant(4')-1a kanamycin resistance gene, Rous sarcoma virus long terminal repeat sequences, HCMV immediate early promoter and an SV40 late polyA sequence.

Another embodiment of the invention is an isolated host cell comprising a vector of the invention. Representative host cell examples include Archaea cells; bacterial cells such as *Streptococci, Staphylococci, Enterococci, E. coli, Streptomyces*, cyanobacteria, *B. subtilis* and *S. aureus*; fungal cells such as *Kluveromyces, Saccharomyces, Basidomycete, Candida albicans* or *Aspergillus*; insect cells such as *Drosophila* S2 and *Spodoptera* Sf9; animal cells such as CHO, COS, HeLa, C127, 3T3, BHK, 293, CV-1, Bowes melanoma and myeloma; and plant cells, such as gymnosperm or angiosperm cells. The host cells in the methods of the invention may be provided as individual cells, or populations of cells. Populations of cells may comprise an isolated or cultured population of cells or cells present in a matrix such as a tissue.

Introduction of a polynucleotide, such as a vector, into a host cell can be done using well known methods (Sambrook et al., Molecular Cloning: A Laboratory Manual, $3^{rd}$ ed., Cold Spring Harbor Laboratory Press, Cold Spring Harbor, N.Y., 2001). Such exemplary methods are calcium phosphate transfection, DEAE-Dextran mediated transfection, microinjection, cationic lipid-mediated transfection, electroporation, and infection.

Another aspect of the invention is an isolated polypeptide comprising a polypeptide having the sequence shown in SEQ ID NO: 1. SEQ ID NO: 1 is a polypeptide comprising the full length cynoCCL17 protein.

Another aspect of the invention is an isolated polypeptide having the sequence shown in SEQ ID NO: 3. SEQ ID NO: 3 is a polypeptide comprising the mature cynoCCL17 protein.

The polypeptides of the invention may be produced by chemical synthesis, such as solid phase peptide synthesis, on an automated peptide synthesizer. Alternatively, the polypeptides of the invention can be obtained from polynucleotides encoding these polypeptides by the use of cell-free expression systems such as reticulocyte lysate based expression systems, wheat germ extract based expression systems, and *Escherichia coli* extract based expression systems. The polypeptides of the invention can also be obtained by recombinant methods using well-known techniques.

The polypeptides of the invention may comprise fusion polypeptides comprising a polypeptide of the invention fused with a second polypeptide. Such second polypeptides may be leader or secretory signal sequences, a naturally occurring pre- or prepro-protein sequence, or partially or completely synthetic sequences. Exemplary fusion proteins can be formed by conjugating a cynoCCL17 polypeptide having an amino acid sequence shown in SEQ ID NO: 1 or 3 and one or more domains derived from an immunoglobulin constant domain, such as a CH1, CH2, and CH3 domain, or an Fc domain. Such constructs are well known in the art as described in e.g. U.S. Pat. Nos. 5,116,964, 5,709,859, PCT. Publ. No. WO04/002417; and PCT Publ. No. WO05/081687.

It is possible to modify the structure of the polypeptides or fragments of the invention for such purposes as enhancing stability, solubility, receptor binding and the like. For example, a modified polypeptide can be produced in which the amino acid sequence has been altered for example by amino acid substitution, deletion, or addition. It is contemplated that an isolated replacement of a leucine with an isoleucine or valine, an aspartate with a glutamate, a threonine with a serine, or a similar replacement of an amino acid with a structurally related amino acid (i.e., conservative mutations) will, in some instances but not all, not have a major effect on the biological activity of the resulting molecule. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981). Whether a change in the amino acid sequence of a polypeptide or fragment thereof results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement has taken place can readily be tested in the same manner.

The polypeptides of the invention can also be formulated in a pharmaceutically acceptable carrier or diluent. A variety of aqueous carriers may be employed, e.g., 0.4% saline, 0.3% glycine and the like. These solutions are sterile and generally free of particulate matter. These solutions may be sterilized by conventional, well-known sterilization techniques (e.g., filtration). The compositions may contain pharmaceutically acceptable auxiliary substances as required to approximate physiological conditions, such as pH adjusting and buffering agents. The concentration of the polypeptides of the invention in such pharmaceutical formulation can vary widely, i.e., from less than about 0.5%, usually at or at least about 1% to as much as 15 or 20% by weight and will be selected primarily based on fluid volumes, viscosities and other factors, according to the particular mode of administration selected.

The polypeptides of the invention can be lyophilized for storage and reconstituted in a suitable carrier prior to use. This technique has been shown to be effective with conventional protein preparations. Lyophilization and reconstitution techniques are well known in the art.

Another embodiment of the invention is a method for expressing a polypeptide comprising the steps of providing a host cell of the invention; culturing the host cell under conditions sufficient for the expression of a polypeptide comprising the sequence shown in SEQ ID NO: 1 or having the sequence shown in SEQ ID NO: 3; and optionally confirming expression of at least one polypeptide comprising the sequence shown in SEQ ID NO: 1 or having the sequence shown in SEQ ID NO: 3.

Host cells can be cultured under any conditions suitable for maintaining or propagating a given type of host cell and sufficient for expressing a polypeptide. Culture conditions, media, and related methods sufficient for the expression of polypeptides are well known in the art. For example, many mammalian cell types can be aerobically cultured at 37° C. using appropriately buffered DMEM media while bacterial, yeast and other cell types may be cultured at 37° C. under appropriate atmospheric conditions in LB media.

In the methods of the invention the expression of a polypeptide can be confirmed using a variety of different techniques well known in the art. For example, expression of a polypeptide can be confirmed using detection reagents, such as antibodies specific for an expressed polypeptide followed by SDS-PAGE or FACS. Antibodies that specifically bind to or cross-react with the cynoCCL17 polypeptides of the invention are one example of such reagents.

Another embodiment of the invention is a polypeptide produced by the methods of invention. Such polypeptides may comprise post-translational modifications including glycosylation or phosphorylation for example. Such polypeptides may also comprise alternative polypeptide forms such as splice variants, truncated forms, or proteolytically modified forms.

Another embodiment of the invention is an antibody that specifically binds a polypeptide of the invention. The polypeptides of the invention can be used to produce polyclonal or monoclonal antibodies against cynoCCL17. Techniques for making murine, chimeric, humanized and fully human monoclonal antibodies using protein or nucleic acid immunization are routine and well known to those skilled in the art. Additional discussion and description of such techniques can be found above.

Another embodiment of the invention is a method of determining cross-reactivity of a CCL17 modulator with *Macaca fascicularis* CCL17. Even if the polypeptides and epitopes are preserved across species and in the species under consideration for a predictive model for a modulator, cross-reactivity of a modulator should be established before additional experimentation is performed (Loisel et al., Crit. Rev. in One. Hematol. 62:34-42, 2007). Cross-reactivity of modulators, antibodies of the invention and other CCL17 antibodies to polypeptides and other antigens may be assayed using, for example, competitive and non-competitive assay systems using techniques such as BIAcore analysis, FACS analysis, immunofluorescence, immunocytochemistry, radioimmunoassays, ELISA, "sandwich" immunoassays, immunoprecipitation assays, western blots, immunoradiometric assays, fluorescent immunoassays, and protein A immunoassays. Such assays are routine and well known in the art (Ausubel et al., eds, 1994, Current Protocols in Molecular Biology, Vol. 1, John Wiley & Sons, Inc., New York). Cross-reactivity can also be evaluated by assaying for a modulation of a biological activity associated with activation of CCL17. For example, cross-reactivity of a human anti-CCL17 antibody with cynoCCL17 polypeptide can be evaluated using an assay assessing effect of the human anti-CCL17 antibody on blocking cynoCCL17 biological activity on cells expressing the CCL17 receptor CCR4. CCR4 may be expressed endogenously on the cells, or in an overexpression system. Human CCR4 or CCR4 from other species may be used. Human CCR4 has an amino acid sequence shown in SEQ ID NO: 9. Exemplary cells that can be used are CCRF-CEM, Jurkat and Hut78 for endogenous expression and L1.2, HEK293 and B300-19 for overexpression of CCR4.

Another embodiment of the invention is a method for determining if a CCL17 modulator is likely to be safe or unsafe for use in humans comprising providing a CCL17 modulator, a first *Macaca fascicularis* monkey, and a second *Macaca fascicularis* monkey; administering the CCL17 modulator to the first *Macaca fascicularis* monkey; and determining whether the first *Macaca fascicularis* monkey is presenting a deleterious symptom relative to the second monkey, where presentation of a deleterious symptom by the first *Macaca fascicularis* monkey shows the CCL17 modulator is potentially unsafe for use in humans and a lack of presentation of a deleterious symptom by the first *Macaca fascicularis* monkey shows the CCL17 therapeutic is potentially safe in humans.

In the methods of the invention the determination of whether the first *Macaca fascicularis* monkey is presenting a deleterious symptom relative to the second *Macaca fascicularis* monkey is readily accomplished. For example, a person of ordinary skill in the art such as a veterinarian, veterinarian's assistant, animal technician, or research scientist can determine if a symptom presented by an animal is deleterious. Examples of deleterious symptoms include death, coma, seizures, fever, organ failure, tissue abnormalities, impaired organ function, impaired tissue function, cancers, tumors, ulcers, bleeding, infections and the like. The CCL17 modulators that can be tested include an antibody, an antibody portion or fragment, a peptide, a polypeptide, an oligonucleotide, a small molecule, or a combination thereof.

The present invention will now be described with reference to the following specific, non-limiting examples.

EXAMPLE 1

Isolation of Polynucleotides Encoding *Macaca fascicularis* CCL17 (CynoCCL17)

Primers were designed from the 5' and 3' untranslated regions of the human CCL17 gene (SEQ ID NO: 6, GenBank Acc. No. NM_002987). PCR was performed using the designed primers (5'UTR1: SEQ ID NO: 11; 3'UTR: SEQ ID NO: 12) and *Macaca fascicularis* testis cDNA (BioChain) as a template. An amplified fragment of about 300 bp was isolated and subcloned using the TOPO-PA kit (Invitrogen, Carlsbad, Calif.) using routine methods. Plasmid DNA from several transformants was isolated and sequenced. The coding region of the cloned cynoCCL17 cDNA was found to be 300 nucleotides long and to encode a predicted protein of 100 amino acids long with a predicted 32 amino acid signal peptide. The identity and similarity between the cyano and human CCL17 proteins is 84% and 89%, respectively. The cynoCCL17 has a nine amino acid insertion in the predicted signal peptide region when compared to the human CCL17. Additionally, a stop codon in the cynoCCL17 3' nucleotide sequence results in a 3 amino acid truncation of the protein when compared to the human CCL17. The closest ortholog of cynoCCL17 is a *Macaca mulatta* (Rhesus monkey) cDNA for CCL17 (SEQ ID NO: 12, GenBank Acc. No. NM_001032852). CynoCCL17 and predicted Rhesus monkey polynucleotides encoding full length CCL17 and full length CCL17 protein are 94.7% and 91% identical, respectively. The cynoCCL17 and the predicted rhesus monkey mature proteins are identical except for the 3 amino acid truncation of the cynoCCL17 C-terminus when compared to the Rhesus.

Figure 1:
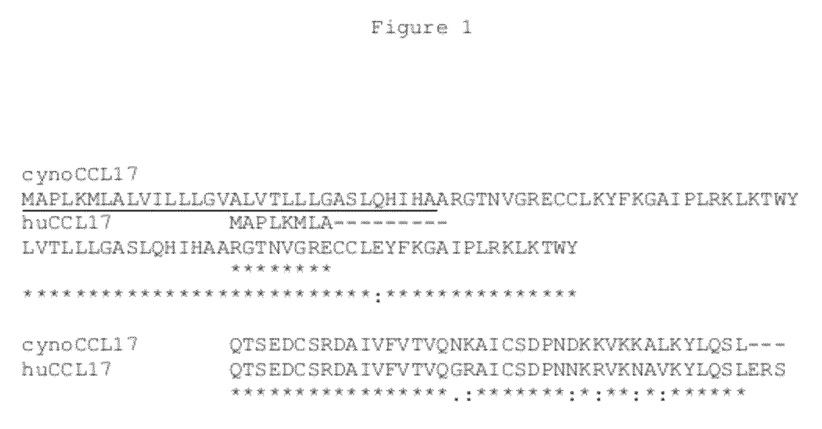
FIG. 1. Protein sequence alignment of *Macaca fascicularis* CCL17 (cynoCCL17) (SEQ ID NO: 1) vs. human CCL17 (SEQ ID NO: 5). Numbering according to cynoCCL17 sequence. Putative signal sequence is underlined.

The alignment between humanCCL17 and the cloned cynoCCL17 polypeptide sequence is shown in FIG. 1.

EXAMPLE 2

CynoCCL17 cDNA Encodes a Functional Protein

Protein expression. cDNA encoding the mature cynoCCL17 (SEQ ID NO: 4) plus a N-terminal methionine was codon optimized (SEQ ID NO: 13) for *E. coli* expression and cloned into a pET24d vector for bacterial expression using standard techniques. The resulting vector was transfected into BL21 (DE3) cells, and the mature cynoCCL17 protein was expressed after IPTG induction as inclusion bodies (IBs). The inclusion bodies (IBs) containing cynoCCL17 were prepared from 33 g of frozen wet bacterial pellet resulted from 6 L shake flask culture. The bacteria pellet was resuspended into 300 mL of lysis buffer (20 mM Tris, pH 8.5, 5 mM EDTA, 100 mM NaCl), and the cells were disrupted by passing twice through a microfluidizer. The IBs were collected by centrifugation at 5000 rpm for 10 min and washed 2 times each with ~200 mL wash buffer (lysis buffer+1% Triton X-100). 4 g wet IB pellet were obtained.

The IBs (4 g wet pellet) were resuspended into 30 mL solubilization buffer containing 8 M urea, 5 mM EDTA, 20 mM Tris HCl, pH 7. The solubilization was performed by constant stirring at room temperature for a duration of 2 hrs. The solubilized IBs was clarified by centrifugation at 4° C./18000 g for 10 min and then loaded onto 2×5 mL HiTrap SP-Sepharose Fast Flow (SPFF) columns connected in tandem. The flow rate was 1 mL/min. The column was then washed with Buffer A (10 mM sodium phosphate, pH 7, 8 M urea) until a flat baseline was achieved. For the elution of the protein, a gradient of 0-100% B (Buffer A plus 1 M NaCl) over 14 CV (140 mL) was applied at a flow rate of 1.5 mL/min. Fractions were collected at 1.5 mL/per fraction. The major peak fractions were pooled and to be refolded. The refolding was initiated by adding the pooled fractions (12 mL) obtained above into 108 mL of refolding buffer prepared in such a way that the refolding matrix contains (final concentration) 0.1 M $NaHCO_3$, 2 M guanidine HCl, 3 mM cysteine and 0.3 mM cystine. The refolding was allowed to proceed at room temperature with gentle stirring (~50 rpm).

The progress of the refolding was monitored by analytical RP-HPLC using 4.6×250 mm C18 reversed phase column. The mobile phase A was $H_2O$/0.1% TFA while phase B was acetonitrile/0.1% TFA. The protein was eluted using a gradient of 25-55% B in 80 min at 0.5 mL/min. The refolding was complete at 63 hrs. The refolding mixture was acidified with acetic acid to pH ~3 and filtered passing a 0.45 μm filter, then loaded onto a 10×250 mm C18 column at a flow rate of 0.8 mL/min. The mobile phase A was $H_2O$/0.1% TFA while phase B was acetonitrile/0.1% TFA. The protein was eluted using a gradient of 25-55% B over 3 column volume at a flow rate of 0.8 mL/min. The fractions in the major peak were pooled and dialyzed against 1XD-PBS using a dialysis cassette with 3,500 MWCO. The dialysate was collected and filtered pass 0.2 μm filter. The refolded purified cynoCCL17 was about 7 kD in a reducing SDS-PAGE. Intact protein mass analysis indicated that the N-terminus of the protein started with Alanine.

Figure 2:
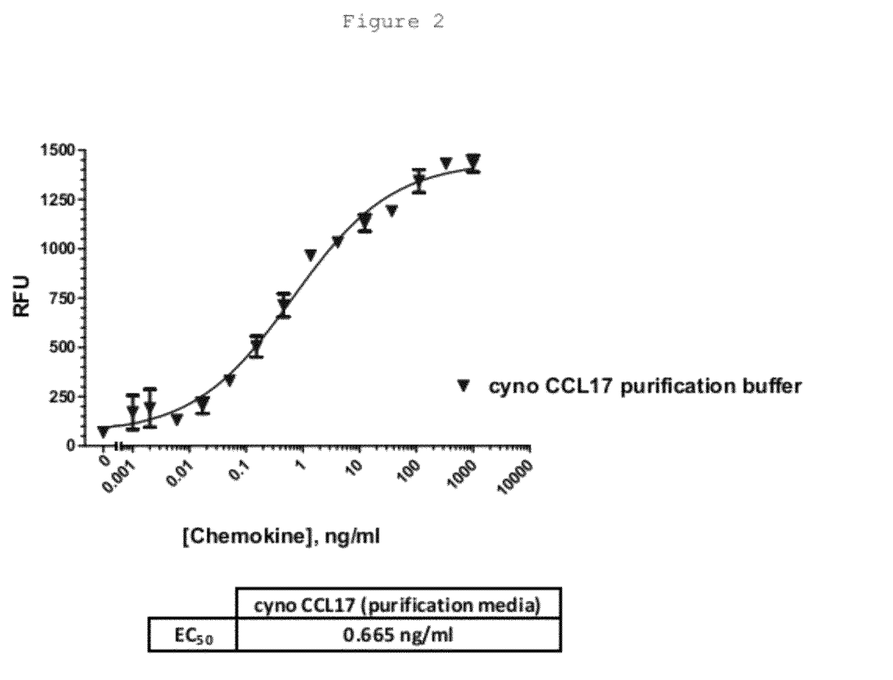
FIG. 2. CynoCCL17-induced calcium flux of CCRF-CEM cells.

Calcium flux. CCRF-CEM cells (ATCC) were plated at 40,000 cells/25 μl into 384-well Poly-D-Lysine coated black white-bottom plates. 25 μl Fluo-8 NW dye in 0.5% pluronic F127 in HBSS was added to the cells. The cells were incubated for 30 min at 37° C. (5% $CO_2$) and for a second 30 min period at room temperature. 12.5 μl CynoCCL17 was added onto the wells in serial dilutions over the range of 5000 ng/ml-3 pg/ml in 0.1% BSA in HBSS. Fluorescence intensity was measured at 490 nm excitation and 525 nm emission using The calculated EC50 was 0.665 ng/ml (FIG. 2).

The present invention now being fully described, it will be apparent to one of ordinary skill in the art that many changes and modifications can be made thereto without departing from the spirit or scope of the appended claims.

The invention claimed is:

1. A fusion protein comprising an isolated Macaca fascicularis polypeptide consisting of the amino acid sequence of SEQ ID NO: 3, wherein the polypeptide is conjugated to a heterologous polypeptide to form a fusion protein having a synthetic sequence.

2. The isolated fusion protein of claim 1, wherein the heterologous polypeptide is an Fc domain.

* * * * *

SEQUENCE LISTING

```
<160> NUMBER OF SEQ ID NOS: 14

<210> SEQ ID NO 1
<211> LENGTH: 100
<212> TYPE: PRT
<213> ORGANISM: Macaca fascicularis
```

<400> SEQUENCE: 1

| Met | Ala | Pro | Leu | Lys | Met | Leu | Ala | Leu | Val | Ile | Leu | Leu | Gly | Val |
| 1 | | | | 5 | | | | | 10 | | | | | 15 |

| Ala | Leu | Val | Thr | Leu | Leu | Leu | Gly | Ala | Ser | Leu | Gln | His | Ile | His | Ala |
| | | | 20 | | | | | 25 | | | | | 30 | | |

| Ala | Arg | Gly | Thr | Asn | Val | Gly | Arg | Glu | Cys | Cys | Leu | Lys | Tyr | Phe | Lys |
| | | | 35 | | | | | 40 | | | | | 45 | | |

| Gly | Ala | Ile | Pro | Leu | Arg | Lys | Leu | Lys | Thr | Trp | Tyr | Gln | Thr | Ser | Glu |
| | 50 | | | | | 55 | | | | | 60 | | | | |

| Asp | Cys | Ser | Arg | Asp | Ala | Ile | Val | Phe | Val | Thr | Val | Gln | Asn | Lys | Ala |
| 65 | | | | | 70 | | | | | 75 | | | | | 80 |

| Ile | Cys | Ser | Asp | Pro | Asn | Asp | Lys | Lys | Val | Lys | Lys | Ala | Leu | Lys | Tyr |
| | | | | 85 | | | | | 90 | | | | | 95 | |

| Leu | Gln | Ser | Leu |
| | | | 100 |

<210> SEQ ID NO 2
<211> LENGTH: 303
<212> TYPE: DNA
<213> ORGANISM: Macaca fascicularis

<400> SEQUENCE: 2

```
atggcccac tgaagatgct ggccctggtc atcctcctcc tgggggttgc cctggtcacc    60
ctcctcctgg gggcttctct gcagcacatc catgcagctc gagggaccaa tgtgggccgg   120
gagtgctgcc tgaagtactt caagggagcc attcccctta aaagctgaa gacgtggtac    180
cagacatccg aggactgttc cagggatgcc attgttttg taactgtcca gaacaaggcc   240
atctgttcgg accccaacga caagaaagtg aagaaggcac ttaaatacct gcaaagcctc   300
tag                                                                  303
```

<210> SEQ ID NO 3
<211> LENGTH: 68
<212> TYPE: PRT
<213> ORGANISM: Macaca fascicularis

<400> SEQUENCE: 3

| Ala | Arg | Gly | Thr | Asn | Val | Gly | Arg | Glu | Cys | Cys | Leu | Lys | Tyr | Phe | Lys |
| 1 | | | | 5 | | | | | 10 | | | | | 15 | |

| Gly | Ala | Ile | Pro | Leu | Arg | Lys | Leu | Lys | Thr | Trp | Tyr | Gln | Thr | Ser | Glu |
| | | | 20 | | | | | 25 | | | | | 30 | | |

| Asp | Cys | Ser | Arg | Asp | Ala | Ile | Val | Phe | Val | Thr | Val | Gln | Asn | Lys | Ala |
| | | | 35 | | | | | 40 | | | | | 45 | | |

| Ile | Cys | Ser | Asp | Pro | Asn | Asp | Lys | Lys | Val | Lys | Lys | Ala | Leu | Lys | Tyr |
| | 50 | | | | | 55 | | | | | 60 | | | | |

| Leu | Gln | Ser | Leu |
| 65 | | | |

<210> SEQ ID NO 4
<211> LENGTH: 207
<212> TYPE: DNA
<213> ORGANISM: Macaca fascicularis

<400> SEQUENCE: 4

```
gctcgaggga ccaatgtggg ccgggagtgc tgcctgaagt acttcaaggg agccattccc    60
cttagaaagc tgaagacgtg gtaccagaca tccgaggact gttccaggga tgccattgtt   120
```

```
tttgtaactg tccagaacaa ggccatctgt tcggaccoca cgacaagaa agtgaagaag    180 gcacttaaat acctgcaaag cctctag                                       207

<210> SEQ ID NO 5
<211> LENGTH: 94
<212> TYPE: PRT
<213> ORGANISM: Homo sapiens

<400> SEQUENCE: 5

Met Ala Pro Leu Lys Met Leu Ala Leu Val Thr Leu Leu Leu Gly Ala
1               5                   10                  15

Ser Leu Gln His Ile His Ala Ala Arg Gly Thr Asn Val Gly Arg Glu
            20                  25                  30

Cys Cys Leu Glu Tyr Phe Lys Gly Ala Ile Pro Leu Arg Lys Leu Lys
        35                  40                  45

Thr Trp Tyr Gln Thr Ser Glu Asp Cys Ser Arg Asp Ala Ile Val Phe
    50                  55                  60

Val Thr Val Gln Gly Arg Ala Ile Cys Ser Asp Pro Asn Asn Lys Arg
65                  70                  75                  80

Val Lys Asn Ala Val Lys Tyr Leu Gln Ser Leu Glu Arg Ser
            85                  90

<210> SEQ ID NO 6
<211> LENGTH: 615
<212> TYPE: DNA
<213> ORGANISM: Homo sapiens
<220> FEATURE:
<221> NAME/KEY: CDS
<222> LOCATION: (130)..(414)

<400> SEQUENCE: 6
gctcagagag aagtgacttt gagctcacag tgtcaccgcc tgctgatggg agagctgaat    60
tcaaaaccag ggtgtctccc tgagcagagg gacctgcaca cagagactcc ctcctgggct   120 cctggcacc atg gcc cca ctg aag atg ctg gcc ctg gtc acc ctc ctc ctg   171
           Met Ala Pro Leu Lys Met Leu Ala Leu Val Thr Leu Leu Leu
           1               5                   10 ggg gct tct ctg cag cac atc cac gca gct cga ggg acc aat gtg ggc     219
Gly Ala Ser Leu Gln His Ile His Ala Ala Arg Gly Thr Asn Val Gly
15                  20                  25                  30 cgg gag tgc tgc ctg gag tac ttc aag gga gcc att ccc ctt aga aag     267
Arg Glu Cys Cys Leu Glu Tyr Phe Lys Gly Ala Ile Pro Leu Arg Lys
                35                  40                  45 ctg aag acg tgg tac cag aca tct gag gac tgc tcc agg gat gcc atc     315
Leu Lys Thr Trp Tyr Gln Thr Ser Glu Asp Cys Ser Arg Asp Ala Ile
            50                  55                  60 gtt ttt gta act gtg cag ggc agg gcc atc tgt tcg gac ccc aac aac     363
Val Phe Val Thr Val Gln Gly Arg Ala Ile Cys Ser Asp Pro Asn Asn
        65                  70                  75 aag aga gtg aag aat gca gtt aaa tac ctg caa agc ctt gag agg tct     411
Lys Arg Val Lys Asn Ala Val Lys Tyr Leu Gln Ser Leu Glu Arg Ser
    80                  85                  90 tga agcctcctca ccccagactc ctgactgtct cccgggacta cctgggacct           464
ccaccgttgg tgttcaccgc ccccaccctg agcgcctggg tccaggggag gccttccagg   524
gacgaagaag agccacagtg agggagatcc catcccttg tctgaactgg agccatgggc    584
acaaagggcc cagattaaag tctttatcct c                                  615

<210> SEQ ID NO 7
```

<211> LENGTH: 94
<212> TYPE: PRT
<213> ORGANISM: Homo sapiens

<400> SEQUENCE: 7

```
Met Ala Pro Leu Lys Met Leu Ala Leu Val Thr Leu Leu Leu Gly Ala
1               5                   10                  15

Ser Leu Gln His Ile His Ala Ala Arg Gly Thr Asn Val Gly Arg Glu
            20                  25                  30

Cys Cys Leu Glu Tyr Phe Lys Gly Ala Ile Pro Leu Arg Lys Leu Lys
        35                  40                  45

Thr Trp Tyr Gln Thr Ser Glu Asp Cys Ser Arg Asp Ala Ile Val Phe
50                  55                  60

Val Thr Val Gln Gly Arg Ala Ile Cys Ser Asp Pro Asn Asn Lys Arg
65                  70                  75                  80

Val Lys Asn Ala Val Lys Tyr Leu Gln Ser Leu Glu Arg Ser
            85                  90
```

<210> SEQ ID NO 8
<211> LENGTH: 28
<212> TYPE: DNA
<213> ORGANISM: Artificial sequence
<220> FEATURE:
<223> OTHER INFORMATION: Oligo for amplifying cynoCCL17 cDNA

<400> SEQUENCE: 8
tcaaaaccag ggtgtctccc tgagcaga                                        28

<210> SEQ ID NO 9
<211> LENGTH: 23
<212> TYPE: DNA
<213> ORGANISM: Artificial sequence
<220> FEATURE:
<223> OTHER INFORMATION: Oligo for amplifying cyno CCL17 cDNA

<400> SEQUENCE: 9
gtctcccggg actacctggg acc                                             23

<210> SEQ ID NO 10
<211> LENGTH: 360
<212> TYPE: PRT
<213> ORGANISM: Homo sapiens

<400> SEQUENCE: 10

```
Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
            20                  25                  30

Gly Ile Lys Ala Phe Gly Glu Leu Phe Leu Pro Pro Leu Tyr Ser Leu
        35                  40                  45

Val Phe Val Phe Gly Leu Leu Gly Asn Ser Val Val Val Leu Val Leu
50                  55                  60

Phe Lys Tyr Lys Arg Leu Arg Ser Met Thr Asp Val Tyr Leu Leu Asn
65                  70                  75                  80

Leu Ala Ile Ser Asp Leu Leu Phe Val Phe Ser Leu Pro Phe Trp Gly
            85                  90                  95

Tyr Tyr Ala Ala Asp Gln Trp Val Phe Gly Leu Gly Leu Cys Lys Met
                100                 105                 110

Ile Ser Trp Met Tyr Leu Val Gly Phe Tyr Ser Gly Ile Phe Phe Val
            115                 120                 125
```

```
Met Leu Met Ser Ile Asp Arg Tyr Leu Ala Ile Val His Ala Val Phe
130                 135                 140
Ser Leu Arg Ala Arg Thr Leu Thr Tyr Gly Val Ile Thr Ser Leu Ala
145                 150                 155                 160
Thr Trp Ser Val Ala Val Phe Ala Ser Leu Pro Gly Phe Leu Phe Ser
                165                 170                 175
Thr Cys Tyr Thr Glu Arg Asn His Thr Tyr Cys Lys Thr Lys Tyr Ser
                180                 185                 190
Leu Asn Ser Thr Thr Trp Lys Val Leu Ser Ser Leu Glu Ile Asn Ile
            195                 200                 205
Leu Gly Leu Val Ile Pro Leu Gly Ile Met Leu Phe Cys Tyr Ser Met
210                 215                 220
Ile Ile Arg Thr Leu Gln His Cys Lys Asn Glu Lys Lys Asn Lys Ala
225                 230                 235                 240
Val Lys Met Ile Phe Ala Val Val Leu Phe Leu Gly Phe Trp Thr
                245                 250                 255
Pro Tyr Asn Ile Val Leu Phe Leu Glu Thr Leu Val Glu Leu Glu Val
                260                 265                 270
Leu Gln Asp Cys Thr Phe Glu Arg Tyr Leu Asp Tyr Ala Ile Gln Ala
            275                 280                 285
Thr Glu Thr Leu Ala Phe Val His Cys Cys Leu Asn Pro Ile Ile Tyr
290                 295                 300
Phe Phe Leu Gly Glu Lys Phe Arg Lys Tyr Ile Leu Gln Leu Phe Lys
305                 310                 315                 320
Thr Cys Arg Gly Leu Phe Val Leu Cys Gln Tyr Cys Gly Leu Leu Gln
                325                 330                 335
Ile Tyr Ser Ala Asp Thr Pro Ser Ser Ser Tyr Thr Gln Ser Thr Met
                340                 345                 350
Asp His Asp Leu His Asp Ala Leu
            355                 360

<210> SEQ ID NO 11
<211> LENGTH: 1083
<212> TYPE: DNA
<213> ORGANISM: Homo sapiens

<400> SEQUENCE: 11
atgaacccca cggatatagc agacaccacc ctcgatgaaa gcatatacag caattactat      60
ctgtatgaaa gtatcccaa gccttgcacc aaagaaggca tcaaggcatt tggggagctc     120
ttcctgcccc cactgtattc cttggttttt gtatttggtc tgcttggaaa ttctgtggtg    180
gttctggtcc tgttcaaata caagcggctc aggtccatga ctgatgtgta cctgctcaac    240
cttgccatct cggatctgct cttcgtgttt tccctccctt tttggggcta ctatgcagca    300
gaccagtggg tttttgggct aggtctgtgc aagatgattt cctggatgta cttggtgggc    360
ttttacagtg gcatattctt tgtcatgctc atgagcattg atagatacct ggcaattgtg    420
cacgcggtgt ttccttgag gcaaggacc ttgacttatg ggtcatcac cagtttggct    480 acatggtcag tggctgtgtt cgcctcccct cctggctttc tgttcagcac ttgttatact    540
gagcgcaacc atacctactg caaaaccaag tactctctca actccacgac gtggaaggtt    600
ctcagctccc tggaaatcaa cattctcgga ttggtgatcc ccttagggat catgctgttt    660
tgctactcca tgatcatcag gaccttgcag cattgtaaaa atgagaagaa gaacaaggcg    720
gtgaagatga tctttgccgt ggtggtcctc ttccttgggt tctggacacc ttacaacata    780
```

```
gtgctcttcc tagagaccct ggtggagcta gaagtccttc aggactgcac ctttgaaaga      840
tacttggact atgccatcca ggccacagaa actctggctt ttgttcactg ctgccttaat      900
cccatcatct acttttttct gggggagaaa tttcgcaagt acatcctaca gctcttcaaa      960
acctgcaggg gccttttgt gctctgccaa tactgtgggc tcctccaaat ttactctgct     1020
gacaccccca gctcatctta cacgcagtcc accatggatc atgatctcca tgatgctctg     1080
tag                                                                    1083
```

<210> SEQ ID NO 12
<211> LENGTH: 94
<212> TYPE: PRT
<213> ORGANISM: Macaca mulatta

<400> SEQUENCE: 12

```
Met Ala Pro Leu Lys Met Leu Ala Leu Val Ile Leu Leu Leu Gly Ala
1               5                   10                  15

Ser Leu Gln His Ile His Ala Ala Arg Gly Thr Asn Val Gly Arg Glu
            20                  25                  30

Cys Cys Leu Lys Tyr Phe Lys Gly Ala Ile Pro Leu Arg Lys Leu Lys
        35                  40                  45

Thr Trp Tyr Gln Thr Ser Glu Asp Cys Ser Arg Asp Ala Ile Val Phe
    50                  55                  60

Val Thr Val Gln Asn Lys Ala Ile Cys Ser Asp Pro Asn Asp Lys Lys
65                  70                  75                  80

Val Lys Lys Ala Leu Lys Tyr Leu Gln Ser Leu Glu Arg Ser
                85                  90
```

<210> SEQ ID NO 13
<211> LENGTH: 285
<212> TYPE: DNA
<213> ORGANISM: Macaca mulatta

<400> SEQUENCE: 13

```
atggccccac tgaagatgct ggccctggtc atcctcctcc tgggggcttc tctgcagcac       60
atccatgcag ctcgagggac caacgtgggc cgggagtgct gcctgaagta cttcaaggga      120
gccattcccc ttagaaagct gaagacgtgg taccagacat ccgaggactg ttccagggat      180
gccattgttt ttgtaactgt ccagaacaag gccatctgtt cggaccccaa cgacaagaaa      240
gtgaagaagg cacttaaata cctgcaaagc cttgagaggt cttga                      285
```

<210> SEQ ID NO 14
<211> LENGTH: 219
<212> TYPE: DNA
<213> ORGANISM: Artificial sequence
<220> FEATURE:
<223> OTHER INFORMATION: Codon optimized cynoCCL17 cDNA

<400> SEQUENCE: 14

```
atggcgcgtg gcaccaacgt gggccgtgaa tgctgcctga atattttaa aggcgcgatt        60 ccgctgcgta aactgaaaac ctggtatcag accagcgaag attgcagccg tgatgcgatt      120
gtgtttgtga ccgtgcagaa caaagcgatt tgcagcgatc cgaacgataa aaaagtgaaa      180
aaagcgctga atatctgca gagcctggaa cgtagctaa                              219
```